United States Patent [19]

Rosen et al.

[11] Patent Number: 5,246,447
[45] Date of Patent: Sep. 21, 1993

[54] IMPACT LITHOTRIPSY

[75] Inventors: David I. Rosen, Peabody; Harry Petschek, Lexington; Stephen P. Dretler, Wayland; Krishna M. Bhatta, Brookline, all of Mass.

[73] Assignees: Physical Sciences, Inc., Andover; General Hospital Corporation, Boston, both of Mass.

[21] Appl. No.: 846,757
[22] Filed: Mar. 5, 1992

Related U.S. Application Data

[63] Continuation of Ser. No. 632,487, Feb. 4, 1991, abandoned, which is a continuation of Ser. No. 314,472, Feb. 22, 1989, abandoned.

[51] Int. Cl.$^5$ ............................................. A61B 17/22
[52] U.S. Cl. ............................. 606/128; 128/24 AA; 604/22; 606/127
[58] Field of Search ................... 128/24 AA, 24 EL; 604/22; 606/127, 128; 367/147

[56] References Cited

U.S. PATENT DOCUMENTS

| | | |
|---|---|---|
| 3,785,282 | 1/1974 | Schmidt-Kloiber et al. . |
| 3,823,717 | 7/1974 | Pohlman et al. ............. 128/24 AA |
| 3,927,675 | 12/1975 | Pohlman et al. ..................... 606/128 |
| 4,191,189 | 3/1980 | Barkan . |
| 4,196,736 | 4/1980 | Watanabe ............................ 606/128 |
| 4,227,532 | 10/1980 | Bluhm et al. ........................ 606/128 |
| 4,548,207 | 10/1985 | Reimels . |
| 4,604,003 | 8/1986 | Oinuma et al. ...................... 606/128 |
| 4,624,253 | 11/1986 | Burns . |
| 4,639,252 | 1/1987 | Kelly et al. .......................... 604/282 |
| 4,686,980 | 8/1987 | Williams et al. . |
| 4,687,471 | 8/1987 | Twandowski et al. . |
| 4,722,340 | 2/1988 | Takayama et al. . |
| 4,737,380 | 4/1988 | Shene . |
| 4,870,953 | 10/1989 | Michael et al. . |
| 4,927,426 | 5/1990 | Dretler . |
| 4,927,427 | 5/1990 | Kriauciunas et al. ................ 606/128 |
| 4,932,954 | 6/1990 | Wondrazek et al. . |
| 4,966,132 | 10/1990 | Nowacki et al. .................... 128/24 A |
| 4,983,877 | 1/1991 | Kashiwara et al. . |
| 5,176,675 | 1/1993 | Watson et al. .......................... 606/3 |

FOREIGN PATENT DOCUMENTS

| | | |
|---|---|---|
| 801472 | 12/1968 | Canada . |
| 317507 | 5/1989 | European Pat. Off. . |
| 3707567 | 9/1987 | Fed. Rep. of Germany . |
| PCT/US91/-00143 | 7/1991 | PCT Int'l Appl. . |

OTHER PUBLICATIONS

Dretler et al., *J. Urology*, 146: 746-750 (Sep. 1991), Conversion of the Electrohydraulic Electrode . . . Case Report.
Bhatta, et al., *J. Urology*, 142: 1110 (1989).
Bhatta, et al., *J. Endourology*, 3(4):433-437 (1989).
Bhatta et al., *J. Urology*, 143: 857-860 (Apr. 1990).
Nishioka et al., *Lasers in the Life Sciences*, 1(3): 231-245 (1987).
U.S. Patent Application 07/808,527 filed on Dec. 16, 1991, Rosen et al., *Shielded Tip Catheter*.
U.S. Patent Applications 07/822,704 filed on Jan. 21, 1992, Rosen et al., *Acoustic Impact Delivery Catheter With End Cap*.
Fair, Harry D., Jr., *In Vitro Destruction of Urinary Calculi by Laser-Induced Stress Waves*, vol. 12, No. 2, Mar.-Apr. 1978.
S. Thomas, J. Pensel, W. Meyer, A. Wondraschek, *The Development of an Endoscopically Applicable Optomechanical Coupler For Laser Induced Shock Wave Lithotripsy* (LISL), Ulm Germany, 1987.

Primary Examiner—Stephen C. Pellegrino
Assistant Examiner—Glenn Danson
Attorney, Agent, or Firm—Kenyon & Kenyon

[57] ABSTRACT

Method and apparatus for fracturing hard deposits such as urinary and biliary stones and atherosclerotic plaque in the human body. A flexible guide having a hard mass capping an end is adapted for insertion through a fluid passage in a living body. An energy source creates a rapid vapor expansion adjacent to the cap causing it to undergo a pulse like movement, imparting a high-velocity impulse to an adjacent deposit, thereby fracturing it. The energy source may be a laser with a fiber optic delivery system in the guide terminating adjacent to the cap to cause vaporization of the mass cap to create the vapor expansion. The energy source may be a spark generator with a conductor associated with the guide to deliver a fluid vaporizing spark adjacent to the mass cap. Other forms of rapid energy delivery such as chemical detonations or ballistic impact may also be applicable.

14 Claims, 2 Drawing Sheets

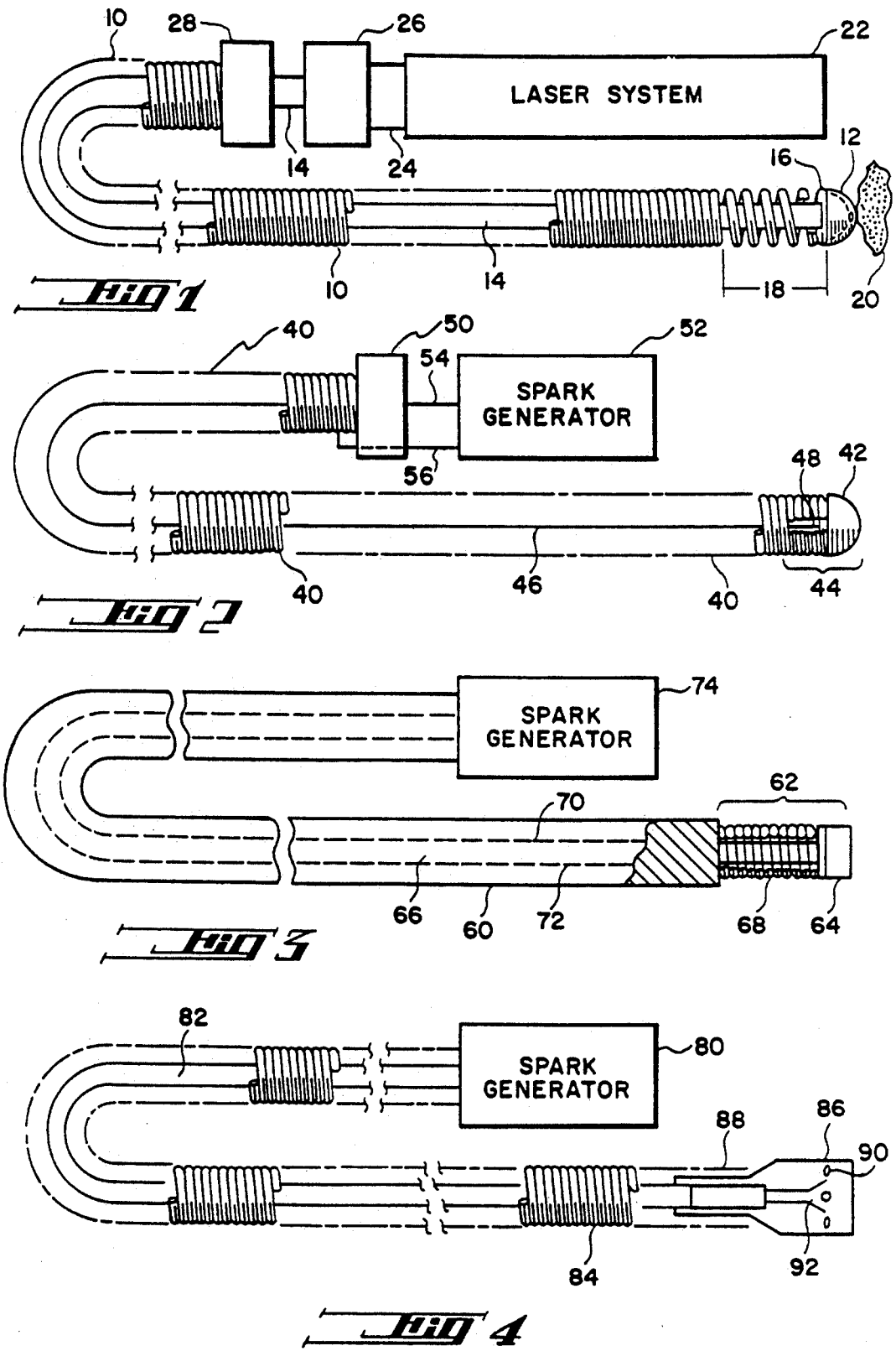

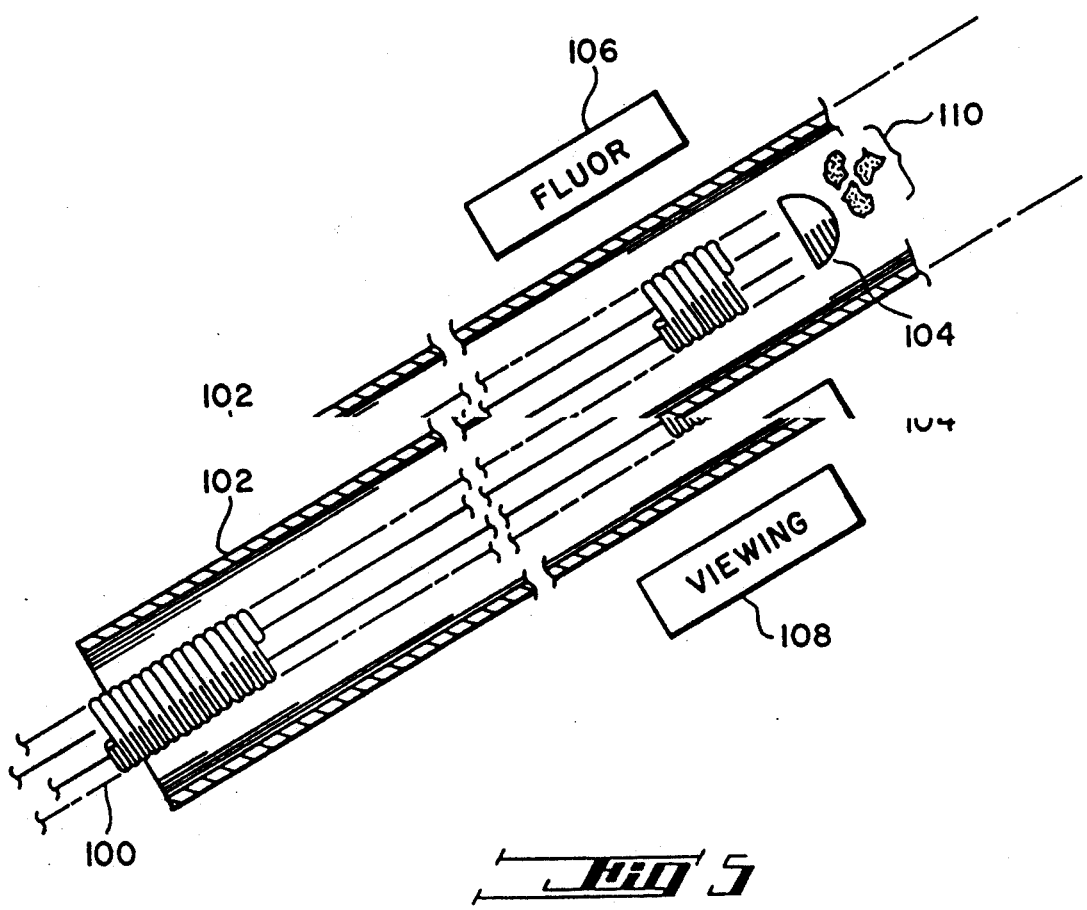
_Fig. 5_
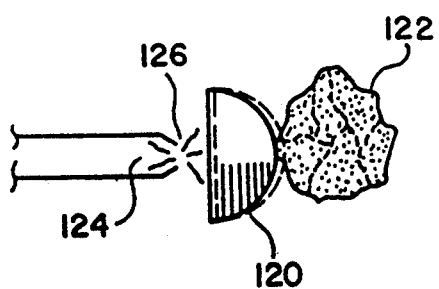
_Fig. 6_

IMPACT LITHOTRIPSY

This is a continuation of application Ser. No. 632,487 filed on Feb. 4, 1991, which is a continuation of application Ser. No. 314,472 filed on Feb. 22, 1989 both now abandoned.

FIELD OF THE INVENTION

The present invention relates to a method and apparatus for fracturing hard formations in the body, and more specifically, to a method and apparatus for transferring energy to the end cap of a flexible guide which imparts a high-velocity impulse to a target deposit thereby fracturing it.

BACKGROUND OF THE INVENTION

Calciferous and similar deposits occur in body fluid passages of various types. Of particular interest are kidney and gall stones as well as arterial plaque.

Radiation in various forms has been used for destroying or removing such deposits from the internal passages of the body. In one form of laser therapy, radiation is directed onto a light-receiving surface of a heat-generating element. The element is then placed in contact with the target deposit, melting it. This approach has several drawbacks which include:

1. thermal damage to surrounding tissue;
2. only fatty plaques readily melt;
3. more advanced fibrous and calcified plaques form char and debris; and
4. the hot element adheres to the tissue rupturing it when the element is removed.

In another approach, laser radiation is applied directly to the target deposit to ablate it or produce shock waves that induce fragmentation. Direct lasertripsy has several disadvantages. Laser energy often damages healthy tissue surrounding the target deposit by direct absorption or by acting as a general heat sink for the high temperature plasma. Some deposits only weakly absorb radiation thereby requiring greater radiation exposure and damage. A sharp laser delivery fiber can cause damage if inadvertently jabbed into healthy tissue.

SUMMARY OF THE INVENTION

The present invention contemplates a method and apparatus for selectively fracturing hard deposits in fluid containing body passages with the impact of small jack hammer like blows from a capped flexible guide inserted through the body passage to the location of a deposit to be fractured.

In implementing the invention, a flexible wire guide terminating with a hard mass or end cap is provided for insertion through a fluid containing body passage. An energy source and delivery system in the flexible guide provide a pulse of energy in the vicinity of the cap to produce a rapid vapor expansion that causes the end cap to undergo a pulse like movement as the vapor expands against the fluid medium of the passage to impart a high-velocity impulse to the target deposit. A means for fluid exchange between the interior and exterior of the apparatus is provided in the end cap region to insure the presence of fluid for increasing the direct impulse against the cap.

In a first embodiment of the invention, the energy source is a pulsed laser and the delivery system is an optical fiber passing through the guide to terminate adjacent to a metal end cap. The laser energy causes vaporization of a small portion of the end cap to create the vapor expansion that drives the end cap forward against the inertia of the fluid.

In a second embodiment, the energy source is a pulsed voltage source and a pair of conductors, one of which may be the wire guide, comprising the delivery system. The conductors terminate in a spark gap adjacent to the end cap. A spark pulse causes fluid vaporization adjacent to the end cap, thereby driving it forward as a reaction.

An advantage of the invention includes the end cap's protection of surrounding healthy tissue from direct laser radiation and thermal radiation from the laser-produced plasma of the vapor expansion which forms against the inside surface of the end cap. A further advantage of the invention is the elimination of inadvertent puncturing of healthy tissue by a sharply pointed laser delivery fiber.

In the laser embodiment, the end cap is fabricated to exhibit good laser absorption providing a reliable, reproducible vapor expansion independent of the absorption characteristics of the target deposit.

DESCRIPTION OF THE DRAWING

The invention will be more fully understood from the following solely exemplary detailed description taken in conjunction with the accompanying drawing, in which;

FIG. 1 is a diagram of one embodiment of the invention which utilizes a laser-produced vapor expansion to drive a hard mass to contact and fragment a target deposit;

FIG. 2 is a diagram of a second embodiment of the invention which utilizes an electrically-produced spark discharge that produces a vapor expansion to drive a hard mass, to contact and fragment a target deposit;

FIG. 3 is a diagram of a variant of the invention of FIG. 2 which utilizes an electrically-produced plasma from a central two wire conductor to drive an internally confined spring-loaded end cap to fragment a target deposit;

FIG. 4 is a diagram of a further variant of the invention of FIG. 2 which utilizes an electrically-produced plasma from a central two wire conductor to drive an internally confined stainless steel end cap with irrigation ports, to contact and fragment a target deposit;

FIG. 5 is a diagram of the fragmentation system of the invention inside a body passage with fragmented target deposits at its distal end and a positioning fluoroscope; and FIG. 6 is a diagram of an end cap of the invention demonstrating the pulse-like advancement of the end cap with subsequent fracturing of the target deposit.

DETAILED DESCRIPTION OF THE INVENTION

The present invention contemplates a method and apparatus for driving a small, hard mass into fracturing, high velocity contact with hard deposits in fluid-containing body passages.

A first embodiment of the invention is illustrated in FIG. 1. A flexible wire guide 10, which typically comprises a commercially available, helically wound French No. 3 guide (0.85-1.00 m diameter) has an end cap 12, the cap and guide are typically of stainless steel or other material which, in response to laser radiation, will vaporize, in a rapid vapor expansion. An optical fiber 14 (typically a 200 micron core) is fed through the wire guide 10 and terminates at a point 16, a short distance from the end cap 12. Laser radiation emanating from the termination 16 strikes the end cap and is absorbed by the metal of the end cap 12, causing vaporization of a small portion of the metal. In actual use, the helical windings of the guide 10 are opened in a terminal portion 18, for example by stretching the last few coils, to facilitate the entry of fluid from body passages, in which the guide is inserted, into the region of the termination 16. The rapid vapor expansion, typically of shock wave nature, generates a forward pressure impulse on the cap 12, in the nature of a miniature jack hammer.

Where the cap 12 has been inserted in a body passage, typically the urethra to a kidney stone, it is capable of fragmenting pieces of the kidney stone, such as the stone 20, to which it comes into contact. The presence of the body fluid creates a mass within the region of the termination 16 where the vapor expansion occurs which confines the expansion and permits a large portion of the energy of the vapor expansion to be directed against the end cap 12 producing a high-velocity, short forward impulse.

The source of radiation applied to the fiber 14 is a laser system 22. Laser system 22 is typically a tunable dye laser. The laser is operated in the mode of producing pulses of approximately 1 microsecond duration and approximately 50 millijoule energy level. Other pulsed laser systems capable of promptly initiating a plasma against the cap and compatible with optical fiber transmission would also be acceptable energy sources. This would include, for example, solid state laser systems such as Alexandrite. A pulsed output beam 24 from the laser 22 is applied to an optical coupling system 26 which in turn applies the pulsed radiation in beam 24 onto optical fiber 14. The fiber 14 passes through a clamp 28 connected to the guide 10 and operative to hold the fiber termination 16 at a predetermined distance from the cap 12. A potting compound near the termination may be used to secure the fiber termination.

A second embodiment of the invention is illustrated in FIG. 2. As shown there a wire guide 40, which may be similar to the guide 10 in FIG. 1 and typically of a size corresponding to French No. 3, terminates in an end cap 42 at a distal end 44 of the wire guide 40. The wire guide is typically helically wound as described before and the termination 44 has helical wires of augmented spacing, for example, by being stretched, to permit the flow of fluid through an interior portion.

A wire conductor 46 is inserted through the wire guide 40, spaced and insulated from the helically wound wires of the guide 40. The inner conductor 46 terminates at a point 48, adjacent to the cap 42. The wire may be held in place by a positioning clamp 50, or potted in place with an adhesive as described above with respect to FIG. 1.

A spark generator 52, which can be a Wolfe 2137.50 or Northgate Research SD1, available in the art, has its output applied on conductors 54 and 56, the conductors are connected to the inner conductor 46 of the guide 40 and the outer helical windings of the guide 40. The spark generator 52 produces an output pulse of up to several microseconds, at several KV and up to 1KA current. The spark generated between the termination 48 of the inner conductor 46 and the end cap 42 causes a vapor expansion of the fluid entering the tip portion 44 and/or the metal of the cap 42 creating a jack hammer like shock impulse movement of the end cap 42, permitting it to fracture calciferous deposits which it contacts.

A different version of the embodiment illustrated in FIG. 2 is shown with respect to FIG. 3. A wire guide 60, typically of the type illustrated above, though not necessarily having a conducting outer shell, has a termination 62 which may be an open helical portion of the wire guide of the prior embodiments. An end cap 64 is applied to the distal end of the wire guide 60. A dual conductor transmission line 66 passes centrally through the wire guide 60 terminating at a point 68 adjacent to the cap 64. The transmission line 66 contains first and second conductors 70 and 72 which terminate to provide a spark gap at the termination 68. The gap is selected to provide, in response to energization from a spark generator 74, of the type illustrated above with respect to FIG. 2, a vaporization of the fluid within the terminal portion 62 generating an impulse motion of the cap 64. A transmission line of the type provided with the above-identified supplier of the spark generator and intended for independent insertion into body passages is suitable for insertion within the guide 60.

FIG. 4 illustrates a further version of the embodiment of FIG. 2. A spark generator 80 is provided, and a two conductor transmission line 82 conducts the output of the spark generator through a guide 84 into a stainless steel end cap 86. The end cap 86 is typically cemented to the distal end 88 of the wire guide 84. Apertures 90 are provided in the end cap 86 to permit body passage fluids to enter the interior of the end cap 86 to a point 92 where the conductors in the transmission cable 92 terminate in a spark gap. The terminal portions of the end cap 86 wire guide 84, where it connects to the end cap 86, are typically resilient enough to permit the impulses generated by the spark from the spark gap 92 termination to drive the end cap 86 forward in jack hammer fashion to permit fracturing of hard deposits to which it is directed.

In actual use, and as illustrated in FIG. 5, a wire guide 100 according to the present invention is inserted through a body passage 102 (natural or surgically created) such as the urethra, for kidney stone fracturing, the biliary duct for gall stone fracturing and an artery for arterial plaque break-up. The end tip 104 of the wire guide 100 is guided by fluoroscopy. An X-ray source 106 and viewing display 108 permit the end of the wire guide 100 to be positioned adjacent to a hard deposit 110 to be fractured as illustrated.

FIG. 6 is an illustration of the dynamics by which an end cap 120 is jack hammered or shock driven forward into a hard deposit 122 by a spark generated by a discharge in a spark gap 126.

Impulse delivery systems other than laser or spark, such as chemical reaction, trigger remotely by signals supplied by a guide, may be used.

It will be understood that all matter herein described or shown in the accompanying drawings is to be interpreted as illustrative only and is not to limit the invention defined in the following claims.

What is claimed is:

1. Apparatus for fracturing hard formations in the body comprising
a flexible guide adapted for insertion through a body passage, said flexible guide having a terminal portion defining an interior space, wherein, when said guide is in an operative position, said terminal portion is located within the body passage,
an end cap movably coupled to said terminal portion, said end cap being adapted for linear reciprocal movement between a first position and a second position linearly spaced from said first position, means for providing fluid access to the interior space of said terminal portion adjacent said end cap, a spark generator operatively connected to said flexible guide for producing a series of sparks, the energy of each spark producing a rapid vaporization of said fluid adjacent a spark gap proximate to said endcap to reciprocally move said end cap from said first position to said second position.

2. An apparatus as set forth in claim 1 wherein said flexible guide comprises a flexible helical wire guide.

3. An apparatus as set forth in claim 2 wherein said means for providing comprises an expanded end of said flexible guide for providing fluid access to an interior of said terminal portion.

4. An apparatus as set forth in claim 1 wherein said spark generator includes a first electrical conductor extending through said guide.

5. An apparatus as set forth in claim 4 further comprising a second electrical conductor which extends through said flexible guide, wherein said spark gap is located at the end of said first and second electrical conductors.

6. An apparatus as set forth in claim 4 wherein said flexible guide includes means for providing electrical conduction from said spark generator to said end cap, said first conductor terminating at a point to form a spark gap with said end cap.

7. An apparatus as set forth in claim 1 wherein said means for providing comprises a plurality of ports in said end cap for providing fluid access to said interior space of said terminal portion through said end cap.

8. An apparatus as set forth in claim 1 wherein said means for providing comprises a plurality of ports in said terminal portion which provide fluid access to said interior space of said terminal portion.

9. An apparatus as set forth in cliam 1 wherein said flexible guide has an outside diameter of 0.85 to 1.00 mm.

10. An apparatus as set forth in claim 1 further including means for returning said end cap to said first position after said end cap has been moved into said second position.

11. An apparatus as set forth in claim 10 wherein said means for returning said end cap to said first position includes a spring coupled between said end cap and said terminal portion.

12. A method for fracturing hard formations in the body comprising:
   inserting a flexible guide having an end cap affixed for reciprocating motion on a terminal portion thereof through a body passage;
   providing fluid to an interior of said terminal portion adjacent said end cap; and
   generating a series of sparks in the fluid adjacent said end cap in the vicinity of a hard formation thereby causing a series of rapid vaporizations of said fluid and a corresponding series of reciprocal mechanical pulse-like movements of said end cap into fracturing contact with said hard formation.

13. The method of claim 12 wherein said generating step includes the step of serially generating sparks through a wire passing through said guide in the fluid adjacent said end cap thereby to power repeated vaporization of a portion of said fluid.

14. A method for impacting formations in the body comprising the steps of:
   inserting a terminal portion of a flexible guide through a body passage, wherein the guide includes an end cap movably coupled to the terminal portion, the end cap being adapted for reciprocal movement between a first position located adjacent to the terminal portion and a second position spaced from the first position, and wherein a fluid is disposed within an interior space of the terminal portion adjacent the end cap, and
   generating a series of sparks across a spark gap disposed within the terminal portion, thereby repeatedly vaporizing the fluid to reciprocally move the end cap from the first position into the second position.

* * * * *